United States Patent [19]

Wise et al.

[11] Patent Number: 5,124,332
[45] Date of Patent: Jun. 23, 1992

[54] SUBSTITUTED INDOLES AS CENTRAL NERVOUS SYSTEM AGENTS

[75] Inventors: Lawrence D. Wise; David J. Wurtrow, both of Ann Arbor, Mich.

[73] Assignee: Warner-Lambert Company, Morris Plains, N.J.

[21] Appl. No.: 647,398

[22] Filed: Jan. 28, 1991

[51] Int. Cl.$^5$ .............. A61K 31/495; C07D 413/00; C07D 403/00; C07D 401/00
[52] U.S. Cl. .................. 514/253; 514/254; 514/256; 514/333; 514/339; 514/899; 544/295; 544/357; 544/333; 544/31; 544/369; 544/370; 544/373; 546/273; 546/256
[58] Field of Search .............. 544/295, 364, 357, 369, 544/370, 373, 333, 405; 546/273, 256; 514/253, 254, 256, 333, 339, 899

[56] References Cited

U.S. PATENT DOCUMENTS 4,954,502  9/1990  Smith et al. ............... 514/253

FOREIGN PATENT DOCUMENTS 345808  12/1989  European Pat. Off.

Primary Examiner—Cecilia Shen
Attorney, Agent, or Firm—Francis J. Tinney

[57] ABSTRACT

Substituted indoles and derivatives thereof are described, as well as methods for the preparation and pharmaceutical composition of the same, which are useful as central nervous system agents and are particularly useful as dopaminergic, antipsychotic, and antihypertensive agents as well as for treating hyperprolactinaemia-related conditions and central nervous system disorders.

7 Claims, No Drawings

SUBSTITUTED INDOLES AS CENTRAL NERVOUS SYSTEM AGENTS

BACKGROUND OF THE INVENTION

The present invention relates to novel substituted indoles and derivatives thereof useful as pharmaceutical agents, to methods for their production, to pharmaceutical compositions which include these compounds and a pharmaceutically acceptable carrier, and to pharmaceutical methods of treatment. The novel compounds of the present invention are central nervous system agents. More particularly, the novel compounds of the present invention are dopaminergic agents.

European Published Patent Application EP 345808-A discloses compounds of Formula I

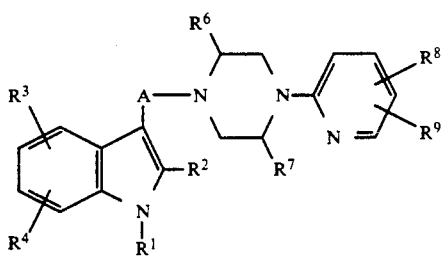

R$^1$, R$^2$=H or 1-4C alkyl;
R$^3$, R$^4$, R$^8$, R$^9$=H, lower alkyl, lower alkoxy, carbamide, halo, CF, or thio-lower alkyl; provided that R$^8$ and R$^9$ are not both H;
A=5-7C cycloalkyl or cycloalkenyl, or —(CH$_2$)$_n$—CHR$^5$—;
n=1, 2, or 3;
R$^5$=R$^1$;
R$^6$, R$^7$=H or Me; or
R$^6$+R$^7$=a methylene bridge;
useful in the treatment of depression, anxiety disorders, panic disorders, obsessive-compulsive disorder, and feeding disorders.

The aforementioned reference does not teach nor suggest the combination of structural variations of the compounds of the present invention nor their use as dopaminergic agents described hereinafter.

SUMMARY OF THE INVENTION

Accordingly, the present invention provides a compound of Formula I

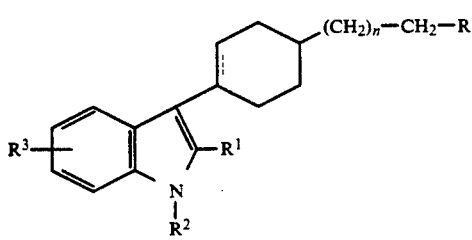

wherein
R is

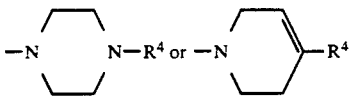

wherein R$^4$ is aryl, unsubstituted or substituted by one to four substituents selected from lower alkyl, lower alkoxy, lower thioalkoxy, hydroxy, lower acyloxy, amino,

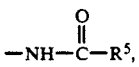

wherein R$^5$ is lower alkyl, halogen, or trifluoromethyl, 2-, 3-, or 4-pyridinyl, unsubstituted or substituted by halogen, lower alkyl, hydroxy, lower acyloxy, lower alkoxy, amino, or

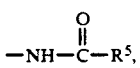

wherein R$^5$ is as defined above, 2-, 4-, or 5-pyrimidinyl, unsubstituted or substituted by halogen, lower alkyl, hydroxy, lower acyloxy, lower alkoxy, amino, or

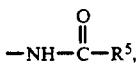

wherein R$^5$ is as defined above, 2-pyrazinyl, unsubstituted or substituted by halogen, lower alkyl, hydroxy, lower acyloxy, lower alkoxy, amino, or

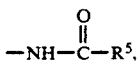

wherein R$^5$ is as defined above, 2- or 3-furanyl, unsubstituted or substituted by halogen, lower alkyl, hydroxy, lower acyloxy, lower alkoxy, amino, or

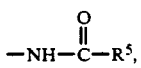

wherein R$^5$ is as defined above, 2-, or 3-thienyl, unsubstituted or substituted by halogen, lower alkyl, hydroxy, lower acyloxy, lower alkoxy, amino, or

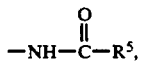

wherein R$^5$ is as defined above, 2-, 4-, or 5-imidazolyl, unsubstituted or substituted by halogen, lower alkyl, hydroxy, lower acyloxy, lower alkoxy, amino, or

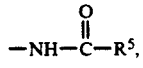

wherein R$^5$ is as defined above, 2-, 4-, or 5-thiazolyl, unsubstituted or substituted by halogen, lower alkyl, hydroxy, lower acyloxy, lower alkoxy, amino, or

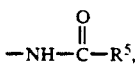

wherein $R^5$ is as defined above, or 2-, 3-, 4-, 5-, 6-, or 7-indolyl, unsubstituted or substituted by halogen, lower alkyl, hydroxy, lower acyloxy, lower alkoxy, amino, or

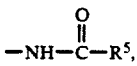

wherein $R^5$ is as defined above;

$R^1$ is hydrogen, —CN, or —CO$_2$H;

$R^2$ is hydrogen, lower alkyl, or cycloalkyl;

$R^3$ is hydrogen, halogen, hydroxyl, lower alkoxy, lower alkyl,

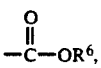

wherein $R^6$ is hydrogen or lower alkyl,

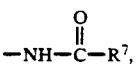

wherein $R^7$ is hydrogen, lower alkyl, cycloalkyl, or aryl, unsubstituted or substituted by one to four substituents selected from lower alkyl, lower alkoxy, lower thioalkoxy, hydroxy, lower acyloxy, amino,

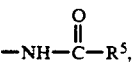

wherein $R^5$ is as defined above, halogen, or trifluoromethyl,

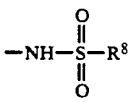

wherein $R^8$ is lower alkyl, cycloalkyl or aryl, unsubstituted or substituted by one to four substituents selected from lower alkyl, lower alkoxy, lower thioalkoxy, hydroxy, lower acyloxy, amino,

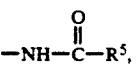

wherein $R^5$ is as defined above, halogen, or trifluoromethyl, or —NH$_2$;

n is zero or an integer of 1, 2, or 3;

$\overline{\phantom{===}}$ is a single or double bond; and corresponding geometric isomers thereof; or a pharmaceutically acceptable acid or base addition salt thereof.

As dopaminergic agents, the compounds of Formula I are useful as antipsychotic agents for treating psychoses such as schizophrenia. They are also useful as antihypertensives and for the treatment of disorders which respond to dopaminergic activation. Thus, other embodiments of the present invention include the treatment, by a compound of Formula I, of hyperprolactinaemia-related conditions, such as galactorrhea, amenorrhea, menstrual disorders and sexual dysfunction, and several central nervous system disorders such as Parkinson's disease, Huntington's chorea, and depression.

A still further embodiment o the present invention is a pharmaceutical composition for administering an effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "lower alkyl" means a straight or branched hydrocarbon radical having from one to six carbon atoms and includes, for example, methyl, ethyl, n-propyl, isopropyl, n-butyl, sec-butyl, isobutyl, tert-butyl, n-pentyl, n-hexyl, and the like.

The term "aryl" means an aromatic radical which is a phenyl group or phenyl group substituted by one to four substituents selected from lower alkyl, lower alkoxy, lower thioalkoxy, hydroxy, lower acyloxy, amino,

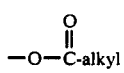

wherein R is lower alkyl, halogen, or trifluoromethyl.

"Lower alkoxy" and "thioalkoxy" are O-alkyl or S-alkyl of from one to six carbon atoms as defined above for "lower alkyl."

"Lower acyloxy" is $$-O-\overset{O}{\underset{\|}{C}}\text{-alkyl}$$

of from one to six carbon atoms as defined above for "lower alkyl".

"Halogen" is fluorine, chlorine, bromine, or iodine.

"Halogen" is fluorine, chlorine, bromine, or iodine.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, magnesium, and the like.

"Noble metal" is platinum, palladium, rhodium, ruthenium, and the like.

The dotted line in a compound of Formula I means a single or double bond.

The compounds of Formula I are capable of further forming both pharmaceutically acceptable acid addition and/or base salts. All of these forms are within the scope of the present invention.

Pharmaceutically acceptable base addition salts of the compounds of Formula I include salts formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, chloine, diethanolamine, ethylenediamine, N-methylglucamine, and procaine (see, for example, Berge, S. M., et al., "Pharmaceutical Salts," *Journal of Pharmaceutical Science*, 66, pp. 1–19 (1977).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent too their respective free acid for purposes of the present invention.

Pharmaceutically acceptable acid addition salts of the compounds of Formula I include salts derived from nontoxic inorganic acids, such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogen phosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phenylacette, citrate, lactate, maleate, tartrate, methanesulfonate, and the like. Also contemplated are salts of amino acids such as arginate and the like and gluconate, galacturonate (see, for example, Berge, S. M., et al, "Pharmaceutical Salts," *Journal of Pharmaceutical Science*, Vol. 66, pages 1-19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention may exist as geometric isomers. Thus, the invention includes the geometric isomers such as cis or trans, E (entgegen) or Z (zusammen), isomers and mixtures thereof. The individual isomers may be prepared or isolated by methods known in the art.

A preferred compound of Formula I is one wherein $R^4$ is aryl, unsubstituted or substituted by one to four substitutents selected from lower alkyl, lower alkoxy, lower thioalkoxy, hydroxy, lower acyloxy, amino,

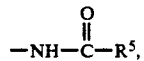

wherein $R^5$ is lower alkyl, halogen, or trifluoromethyl, 2-, 3-, or 4-pyridinyl, 2-, 4-, or 5-pyrimidinyl, 2-, or 3-furanyl, 2-, or 3-thienyl, 2-, 4-, or 5-thiazolyl, or 2-, 3-, 4-, 5-, 6-, or 7-indolyl.

Another preferred embodiment is a compound of Formula I wherein $R^4$ is aryl, 2-, 3- or 4-pyriudinyl, 2-, 4-, or 5-pyrimidinyl, 2-, or 3-furanyl, 2-, or 3-thienyl, 2-, 4-, or 5-thiazolyl, or 2-, 3-, 4-, 5-, 6-, or 7-indolyl.

Particularly preferred compounds are:
Trans 3-[4-[2-[4-(2-pyridinyl)-1-piperazinyl]ethyl]cyclohexyl]-1H-indole;
Cis 3-[4-[2-[4-(2-pyridinyl)-1-piperazinyl]-ethyl]cyclohexyl]-1H-indole;
Trans 3-[4-[2-[4-(2-pyrimidinyl)-1-piperazinyl]-ethyl]cyclohexyl]-1H-indole, hydrochloride;
Cis 3-[4-[2-[4-(2-pyrimidinyl)-1-piperazinyl]ethyl]cyclohexyl]-1H-indole, hydrochloride;
Trans 3-[4-[2-(3,6-dihydro-4-phenyl-1(2H)-pyridinyl)ethyl]cyclohexyl]-1H-indole;
Cis 3-[4-[2-(3,6-dihydro-4-phenyl-1(2H)pyridinyl)ethyl]cyclohexyl]-1H-indole;
Trans 3-[4-[2-(3,6-dihydro-4-(2-thienyl)-1(2H)-pyridinyl)ethyl]cyclohexyl]-1H-indole;
Cis 3-[4-[2-(3,6-dihydro-4-(2-thienyl)-1(2H)-pyridinyl)ethyl]cyclohexyl]-1H-indole;
Trans 3-[4-[2-(3,6-dihydro-4-(2-pyridinyl)-1(2H)-pyridinyl)ethyl]cyclohexyl]-1H-indole;
Cis 3-[4-[2-(3,6-dihydro-4-(2-pyridinyl)-1(2H)-pyridinyl)ethyl]cyclohexyl]-1H-indole;
Trans 5-methoxy-3-[4-[2-[4-(2-pyridinyl)-1-piperazinyl]ethyl]cyclohexyl]-1H-indole;
Cis 5-methoxy-3-[4-[2-[4-(2-pyridinyl)-1-piperazinyl]ethyl]cyclohexyl]-1H-indole;
Trans 5-fluoro-3-[4-[2-[4-(2-pyridinyl)-1-piperazinyl]ethyl]cyclohexyl]-1H-indole;
Cis 5-fluoro-3-[4-[2-[4-(2-pyridinyl)-b 1-piperazinyl]ethyl]cyclohexyl]-1H-indole;
Trans 3-[4-[4-(2-pyridinyl)-1-piperazinylmethyl]cyclohexyl]-1H-indole;
Cis 3-[4-[4(2-pyridinyl)-1-piperazinylmethyl]cyclohexyl]-1H-indole;
3-[4-[2-[4-[(2-Pyridinyl)-1-piperazinyl]ethyl]cyclohexen-1-yl]-1H-indole;
Trans 3-[4-[2-[4-(2-pyridinyl)-1-piperazinyl]ethyl]cyclohexyl]-1H-indol-5-ol;
Cis 3-[4-[2-[4-(2-pyridinyl)-1-piperazinyl]ethyl]cyclohexyl]-1H-indol-5-ol;
Trans 1-methyl-3-[4-[2-[4-(2-pyridinyl)-1-piperazinyl]ethyl]cyclohexyl]-1H-indole; and
Cis 1-methyl-3-[4-[2-[4-(2-pyridinyl)-1-piperazinyl]ethyl]cyclohexyl]-1H-indole;
or a pharmaceutically acceptable acid or base addition salt thereof.

The compounds of Formula I are valuable dopaminergic agents. The tests employed indicate that compounds of Formula I possess dopaminergic activity. Thus, the compounds of Formula I were tested for their ability to inhibit locomotor activity in mice according to the assay described by J. R. McLean, et al, *Pharmacology, Biochemistry and Behavior*, Volume 8, pages 97-99 (1978); and for their ability to inhibit [$^3$H]-spiroperidol binding in a receptor assay described by D. Grigoriadis and P. Seman, *Journal of Neurochemistry*, Volume 44, pages 1925-1935 (1985). The above test methods are incorporated herein by reference. The data in the table show the dopaminergic activity of representative compounds of Formula I.

Biological Activity of Compounds of Formula I

| Example Number | Compound | Inhibition of Locomotor Activity in Mice ED$_{50}$, mg/kg, IP | Inhibition of [$^3$H]Spiroperidol Binding IC$_{50}$, nM |
|---|---|---|---|
| 1 | Trans 3-[4-[2-[4-(2-pyridinyl)-1-piperazinyl]ethyl]cyclohexyl]-1H-indole | 1.4 | 69.8 |
| 2 | Cis 3-[4-[2-[4-(2-pyridinyl)-1-piperazinyl]ethyl]cyclohexyl]-1H-indole | 4.7 | 193 |
| 3 | Trans 3-[4-[2-[4-(2-pyrimidinyl)-1-piperazinyl]ethyl]cyclohexyl]-1H-indole hydrochloride | 3.3 | 224 |
| 4 | Cis 3-[4-[2-[4-(2-pyrimidinyl)-1-piperazinyl]ethyl]cyclohexyl]-1H-indole, hydrochloride | 8.6 | 349 |
| 5 | Trans 3-[4-[2-(3,6-dihydro-4-phenyl-1(2H)-pyridinyl)ethyl]cyclohexyl]-1H-indole | 9.00 | 12.1 |
| 6 | Cis 3-[4-[2-(3,6-dihydro-4-phenyl-1(2H)-pyridinyl)ethyl]cyclohexyl]-1H-indole | 16.6 | 39.3 |
| 7 | Trans 3-[4-[2-(3,6-dihydro-4-(2-thienyl)-1(2H)-pyridinyl)ethyl]cyclohexyl]-1H-indole | 11.7 | 878 |
| 16 | 3-[4-[2-[4-[(2-pyridinyl)-1-piperazinyl]ethyl]cyclohexen-1-yl]-1H-indole | 6.25 | 270 |

SCHEME I

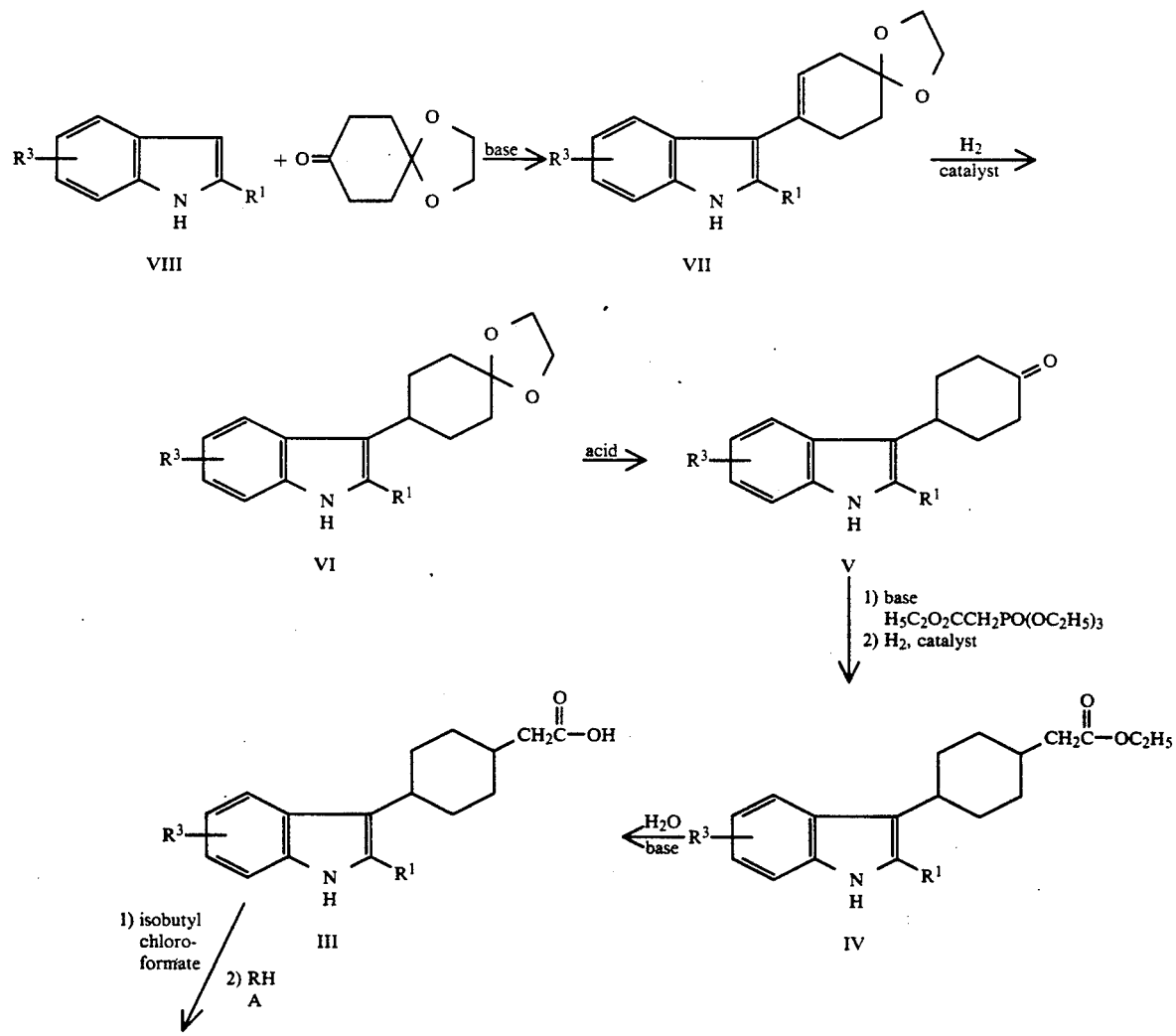

-continued
SCHEME I
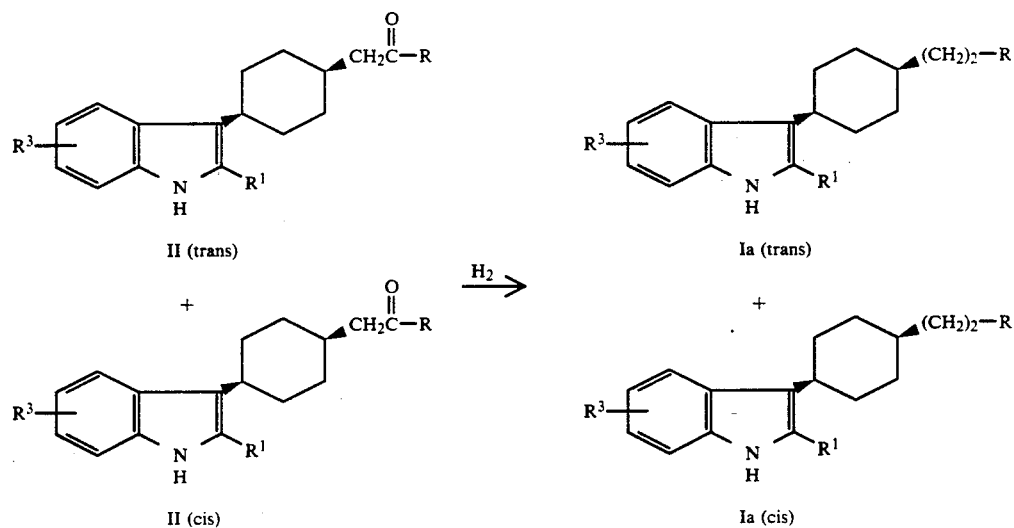
SCHEME II
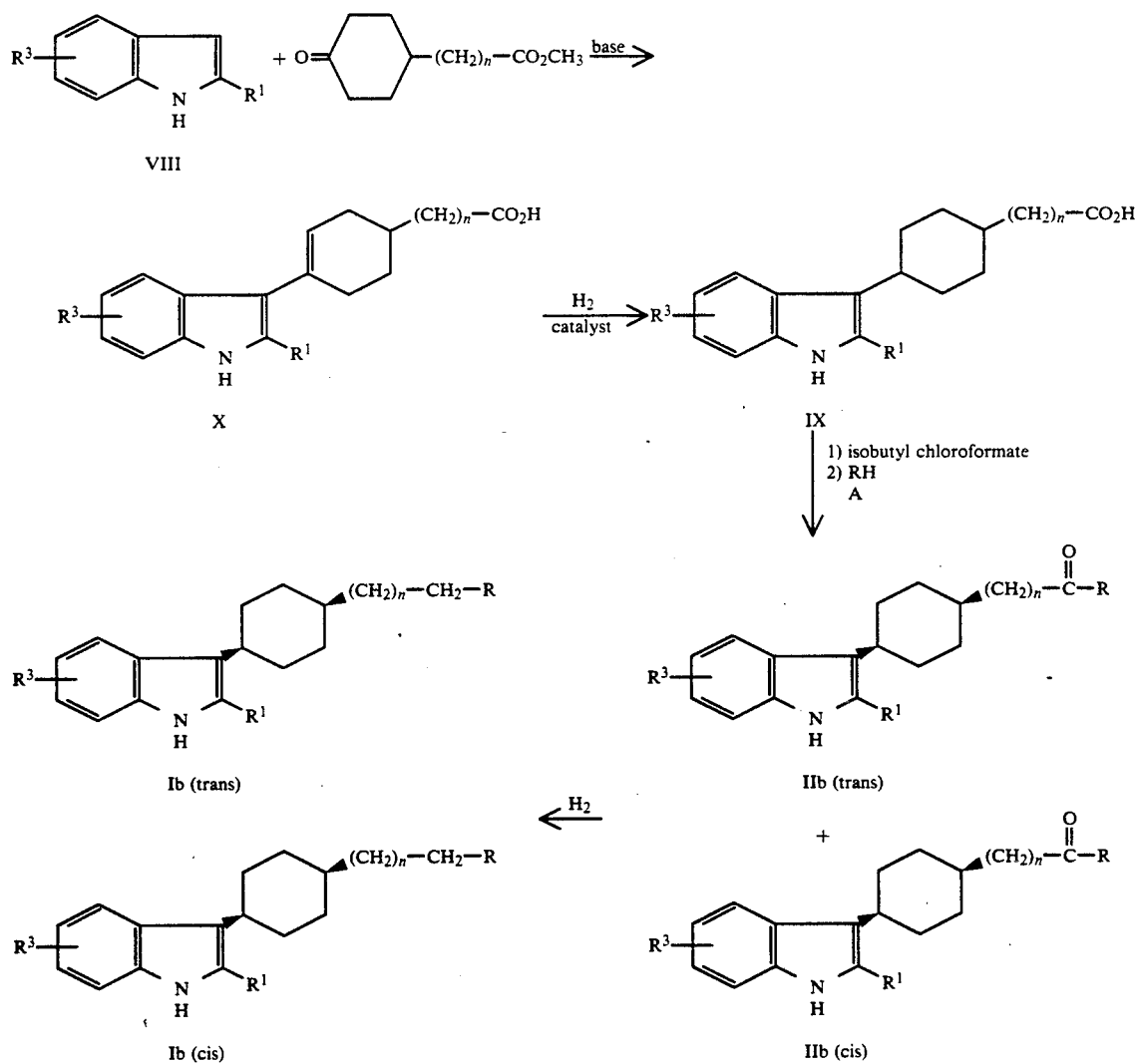

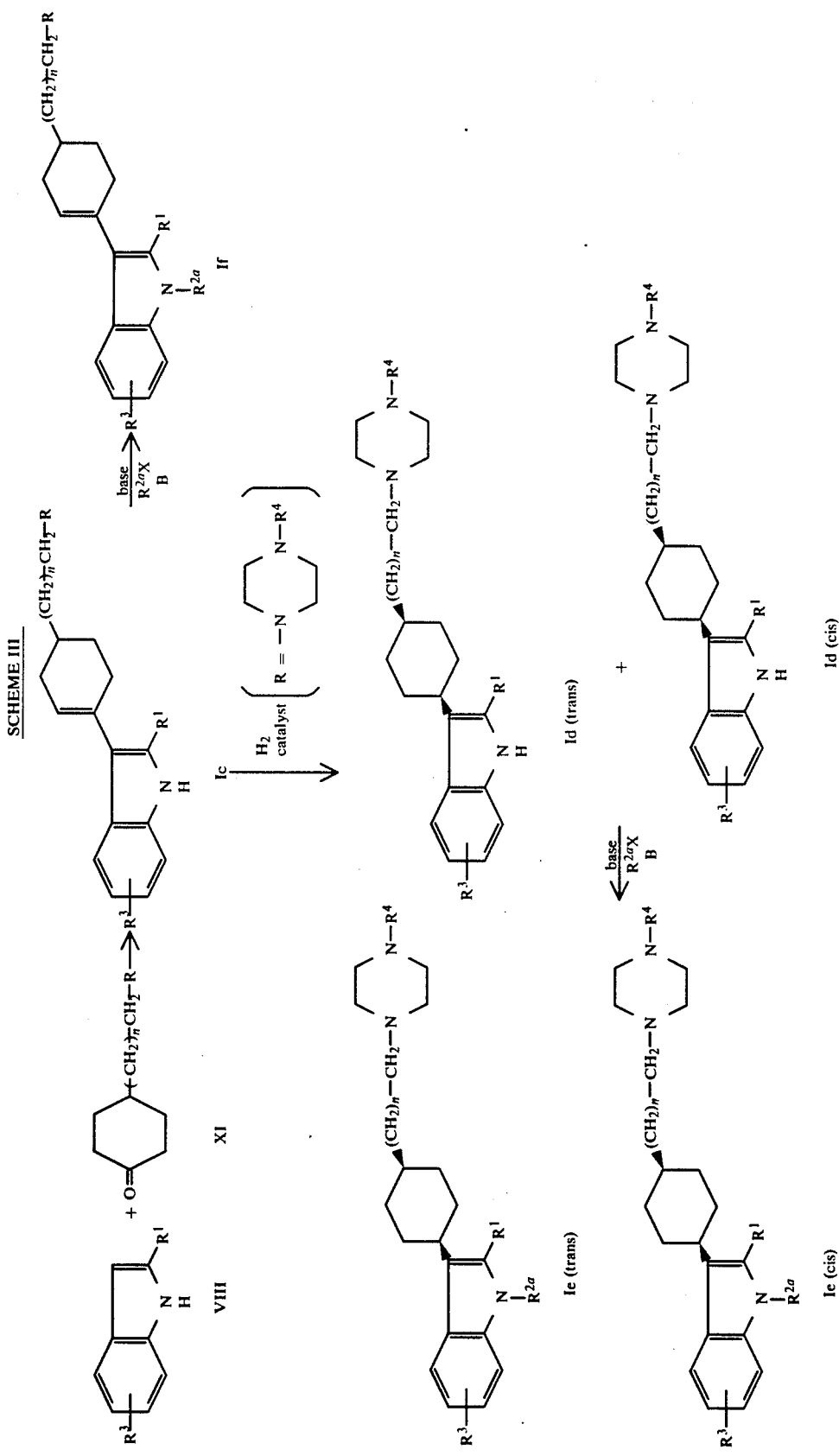

SCHEME IV
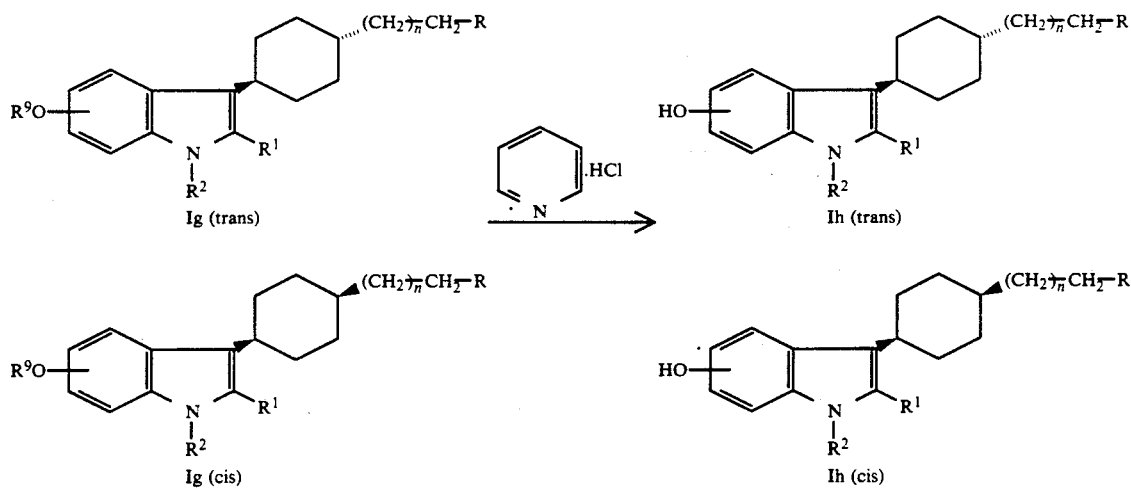

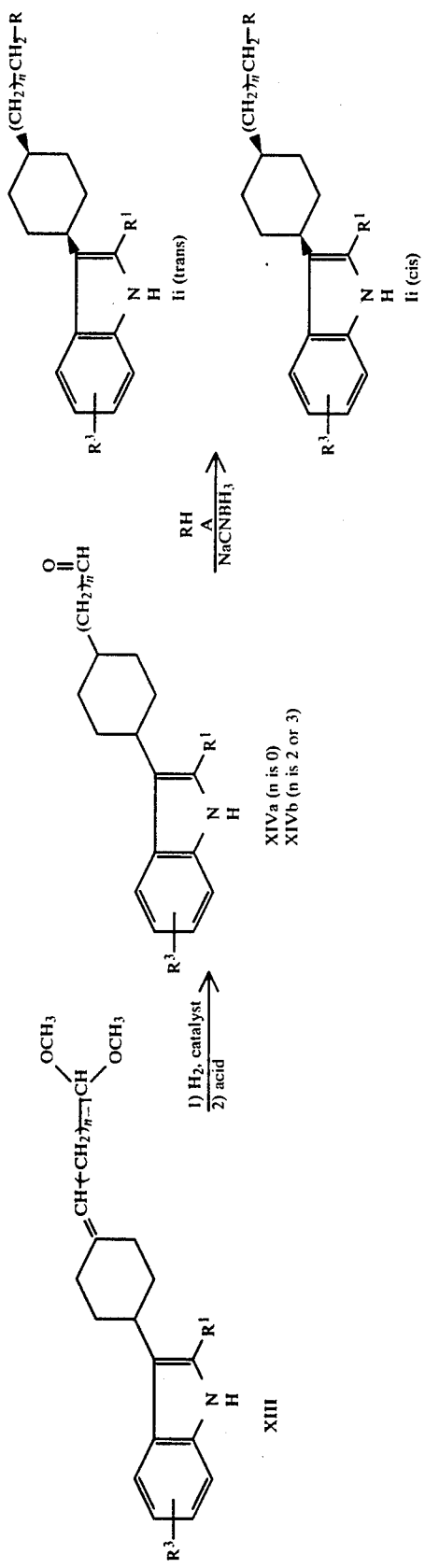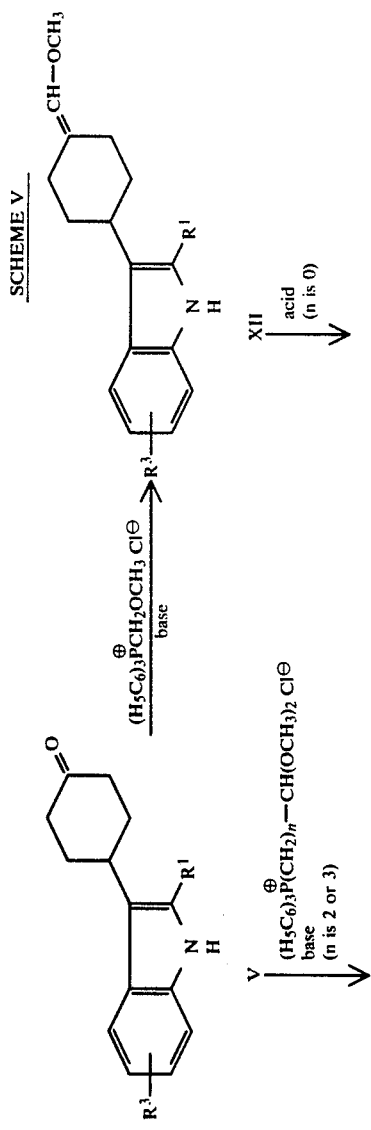

A compound of Formula Ia

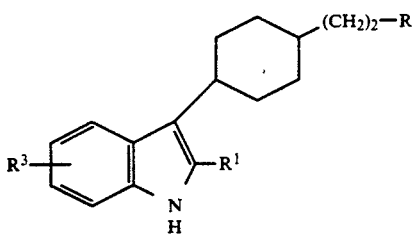

Ia wherein
R is

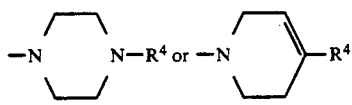

wherein $R^4$ is aryl, unsubstituted or substituted by one to four substituents selected from lower alkyl, lower alkoxy, lower thioalkoxy, hydroxy, lower acyloxy, amino,

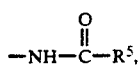

wherein $R^5$ is lower alkyl, halogen, or trifluoromethyl, 2-, 3-, or 4-pyridinyl, unsubstituted or substituted by halogen, lower alkyl, hydroxy, lower acyloxy, lower alkoxy, amino, or

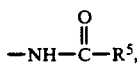

wherein $R^5$ is as defined above, 2-, 4-, or 5-pyrimidinyl, unsubstituted or substituted by halogen, lower alkyl, hydroxy, lower acyloxy, lower alkoxy, amino, or

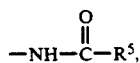

wherein $R^5$ is as defined above, 2-pyrazinyl, unsubstituted or substituted by halogen, lower alkyl, hydroxy, lower acyloxy, lower alkoxy, amino, or

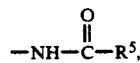

wherein $R^5$ is as defined above, 2- or 3-furanyl, unsubstituted or substituted by halogen, lower alkyl, hydroxy, lower acyloxy, lower alkoxy, amino, or

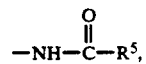

wherein $R^5$ is as defined above, 2-, or 3-thienyl, unsubstituted or substituted by halogen, lower alkyl, hydroxy, lower acyloxy, lower alkoxy, amino, or

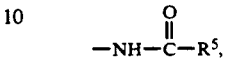

wherein $R^5$ is as defined above, 2-, 4-, or 5-imidazolyl, unsubstituted or substituted by halogen, lower alkyl, hydroxy, lower acyloxy, lower alkoxy, amino, or

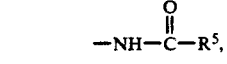

wherein $R^5$ is as defined above, 2-, 4-, or 5-thiazolyl, unsubstituted or substituted by halogen, lower alkyl, hydroxy, lower acyloxy, lower alkoxy, amino, or

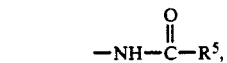

wherein $R^5$ is as defined above, or 2-, 3-, 4-, 5-, 6-, or 7-indolyl, unsubstituted or substituted by halogen, lower alkyl, hydroxy, lower acyloxy, lower alkoxy, amino, or

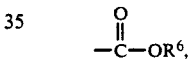

wherein $R^5$ is as defined above;
$R^1$ is hydrogen, —CN, or —CO$_2$H;
$R^3$ is hydrogen, halogen, hydroxyl, lower alkoxy, lower alkyl,

wherein $R^6$ is hydrogen or lower alkyl,

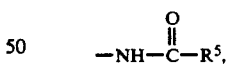

wherein $R^7$ is hydrogen, lower alkyl, cycloalkyl, or aryl, unsubstituted or substituted by one to four substituents selected from lower alkyl, lower alkoxy, lower thioalkoxy, hydroxy, lower acyloxy, amino,

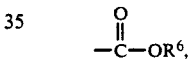

wherein $R^5$ is as defined above, halogen, or trifluoromethyl,

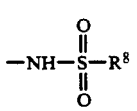

wherein $R^8$ is lower alkyl, cycloalkyl or aryl, unsubstituted or substituted by one to four substituents selected from lower alkyl, lower alkoxy, lower thioalkoxy, hydroxy, lower acyloxy, amino,

wherein $R^5$ is as defined above, halogen, or trifluoromethyl, or —NH$_2$;
and corresponding geometric isomers thereof; or a pharmaceutically acceptable acid or base addition salt thereof is prepared as outlined in Scheme I.

Thus, a compound of Formula VIII wherein $R^1$ is $R^3$ are as defined above is reacted with 1,4-cyclohexanedione monoethylene ketal in the presence of a base such as, for example, an alkali metal hydroxide, alkali metal alkoxide and the like such as, for example, potassium hydroxide, sodium methoxide and the like and a solvent such as, for example, a lower alkyl alcohol such as methanol and the like at about 25° C. to about the reflux temperature of the solvent to afford a compound of formula VII wherein $R^1$ and $R^3$ are as defined above. Preferably the reaction is carried out with potassium hydroxide in refluxing methanol.

A compound of Formula VII is treated with hydrogen in the presence of a catalyst such as a noble metal, for example, palladium on carbon and the like in a solvent such as, for example, tetrahydrofuran, methanol and the like and mixtures thereof at about 0° C. to about 70° to afford a compound of Formula VI wherein $R^1$ and $R^3$ are as defined above. Preferably the reaction is carried out with 5% palladium on carbon in a mixture of tetrahydrofuran and methanol at room temperature.

A compound of Formula VI is treated with an acid such as, for example, an aqueous solution of hydrochloric acid and the like in a solvent such as, for example, acetone and the like at about 0° C. to about 50° C. to afford a compound of Formula V wherein $R^1$ and $R^3$ are as defined above. Preferably the reaction is carried out with a 10% aqueous solution of hydrochloric acid in acetone at room temperature. A solution of a compound of Formula V in a solvent such as, for example, tetrahydrofuran and the like is added to a ylide formed from triethyl phosphonoacetate and sodium hydride in a solvent such as, for example, tetrahydrofuran and the like at about 0° C. to about 50° C. followed by treatment of the resulting intermediate with hydrogen in the presence of a catalyst such as a noble metal, for example, palladium on carbon and the like in a solvent such as, for example, ethanol and the like at about 0° C. to about 50° C. to afford a compound of Formula IV wherein $R^1$ and $R^3$ are as defined above as a mixture of cis and trans isomers. Preferably the reaction is carried out in tetrahydrofuran at room temperature followed by treatment with hydrogen in the presence of 5% palladium on carbon in ethanol at room temperature.

A compound of Formula IV is hydrolyzed in the presence of a base such as, for example, an alkali hydroxide such as, for example, sodium hydroxide and the like and a solvent such as, for example, ethanol at about 0° C. to about the reflux temperature of the solvent to afford a compound of Formula III wherein $R^1$ and $R^3$ are as defined above as a mixture of cis and trans isomers. Preferably the mixture is carried out with a 10% aqueous solution of sodium hydroxide in ethanol at room temperature.

A compound of Formula III is treated with isobutyl chloroformate in the presence of a base such as, for example, triethylamine and a solvent such as, for example, dichloromethane at about —10° C. to about 25° C. followed by reaction with a compound of Formula A

RH      A wherein R is as defined above to afford a compound of Formula II wherein R, $R^1$, and $R^3$ are as defined above as a mixture of cis and trans isomers which are separated into the individual cis and trans isomers by conventional methodology such as, for example, chromatography on silica gel. Preferably the reaction is carries out in the presence of triethylamine in dichloromethane at 0° C. followed by separation of the cis and trans isomers using silica gel chromatography and elution with mixtures of methanol in chloroform.

A compound of either Formula II (trans) or Formula II (cis) is reacted with a hydride reagent such as, for example, lithium aluminum hydride and aluminum chloride and the like in the presence of a solvent such as, for example, tetrahydrofuran and the like at about 0° C. to about 50° C. to afford either a compound of Formula Ia (trans) or a compound of Formula Ia (cis) wherein R, $R^1$, and $R^3$ are as defined above, preferably the reaction is carried out with lithium aluminum hydride and aluminum chloride in tetrahydrofuran at room temperature.

A compound of Formula Ib (trans) or Formula Ib (cis)

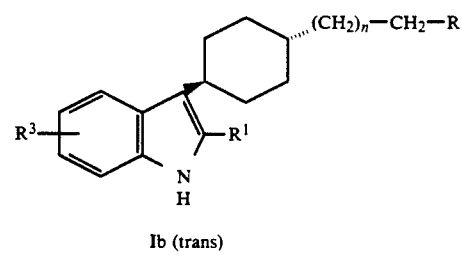

Ib (trans)

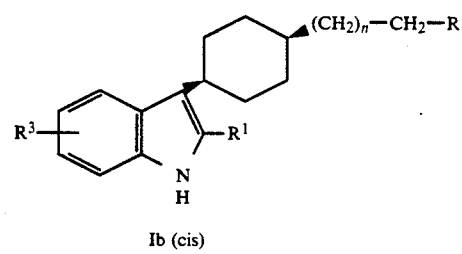

Ib (cis)

wherein R, $R^1$, $R^3$, and n are as defined above or a pharmaceutically acceptable acid or base addition salt thereof is prepared as outlines in Scheme II.

Thus, a compound of Formula VIII is reacted with methyl 4-oxocyclohexanecarboxylate using the methodology used to prepare a compound of Formula VII from a compound of Formula VIII to afford a compound of Formula X wherein $R^1$, $R^3$, and n are as defined above.

A compound of Formula X is converted to a compound of Formula IX wherein $R^1$, $R^3$, and n are as defined above as a mixture of cis and trans isomers using the methodology used to prepare a compound of Formula VI from a compound of Formula VII.

A compound of Formula IX as a mixture of cis and trans isomers is converted to a compound of Formula IIb wherein R, $R^1$, $R^3$, and n are as defined above as a mixture of cis and trans isomers using the methodology used to prepare a compound of II from a compound of Formula III. The cis and trans isomers of a compound of Formula IIb are separated as previously described using silica gel chromatography.

A compound of Formula IIb (trans) or a compound of Formula IIb (cis) is converted to a compound of Formula Ib (trans) or a compound of Formula Ib (cis)

respectively wherein R, $R^1$, $R^3$, and n are as defined above using the methodology used to prepare a compound of Formula Ia (trans) or a compound of Formula Ia (cis) from a compound of Formula II (trans) or a compound of formula II (cis), respectively.

A compound of Formula Ic

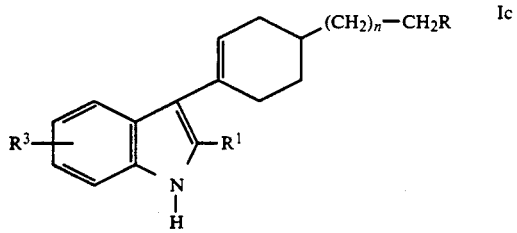

wherein R, $R^1$, $R^3$, and n are as defined above or a pharmaceutically acceptable acid or base addition salt thereof is prepared as outlines in Scheme III.

Thus, a compound of Formula VIII is reacted with a compound of Formula XI wherein R and n are as defined above using the methodology used to prepare a compound of Formula VII from a compound of Formula VIII to afford a compound of Formula Ic.

A compound of Formula Id (trans) or Formula Id (cis)

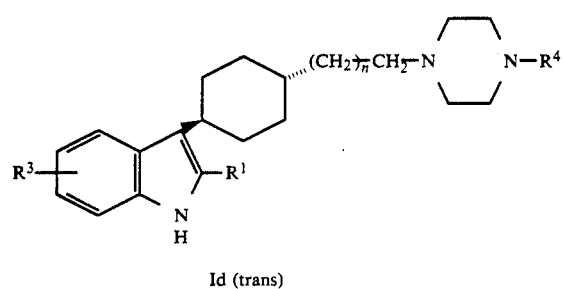

Id (trans)

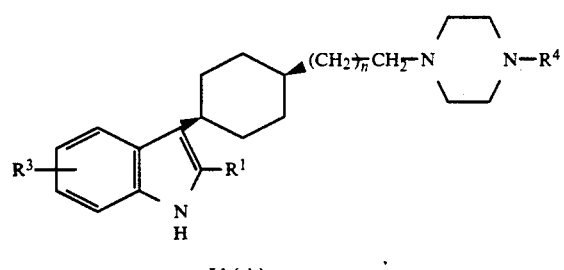

Id (cis)

wherein $R^4$, $R^1$, $R^3$, and n are as defined above or a pharmaceutically acceptable acid or base addition salt thereof is prepared as outlined in Scheme III.

Thus, a compound of Formula Ic-1

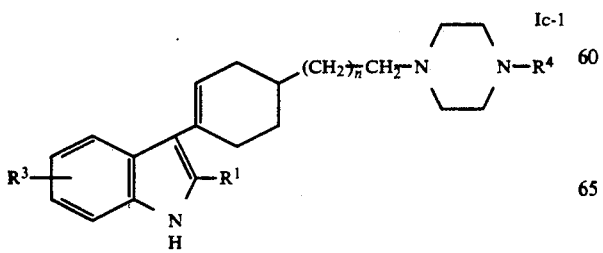

wherein $R^4$, $R^1$, $R^3$, and n are as defined above is converted to a compound of Formula Id as a mixture of cis and trans isomers using the methodology used to prepare a compound of Formula VI from a compound of Formula VII. The cis and trans isomers of a compound of Formula Id are separated as previously described using silica gel chromatography.

A compound of Formula Ie (trans) or Formula Ie (cis)

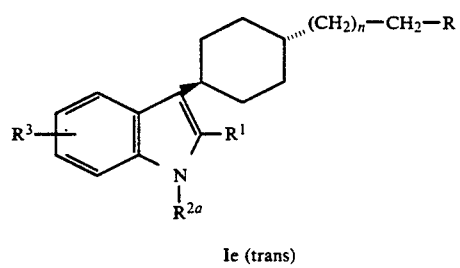

Ie (trans)

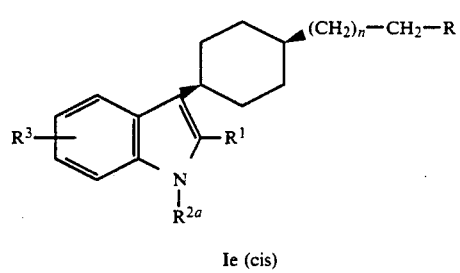

Ie (cis)

wherein $R^{2a}$ is lower alkyl or cycloalkyl and R, $R^1$, $R^3$, and n are as defined above or a pharmaceutically acceptable acid or base addition salt thereof is prepared as outlined in Scheme III.

Thus, a compound of Formula Id (trans) or Formula Id (cis) is reacted with a compound of Formula B $$R^{2a}X \qquad \qquad B$$

wherein X is a halogen or a leaving group such as, for example, arylsulfonyloxy, alkylsulfonyloxy, trihaloalkylsulfonyloxy and the like, for example, methanesulfonyloxy, trifluoromethanesulfonyloxy and the like and $R^{2a}$ is as defined above in the presence of a base such as, for example, potassium hydride and the like and a solvent such as, for example, tetrahydrofuran and the like at about 0° C. to about 50° C. to afford a compound of Formula Ie (trans) or a compound of Formula Ie (cis), respectively. Preferably the reaction is carried out in tetrahydrofuran in the presence of potassium hydride.

A compound of Formula If

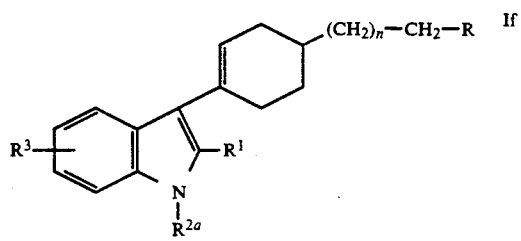

wherein R, $R^1$, $R^{2a}$, $R^3$, and n are as defined above or a pharmaceutically acceptable acid or base addition salt thereof is prepared as outlined in Scheme III.

Thus, a compound of Formula Ic is converted to a compound of Formula If using the methodology used to prepare a compound of Formula Ie (trans) or Formula Ie (cis) from a compound of Formula Id (trans) or Formula Id (cis).

A compound of Formula Ih (trans) or Formula Ih (cis)

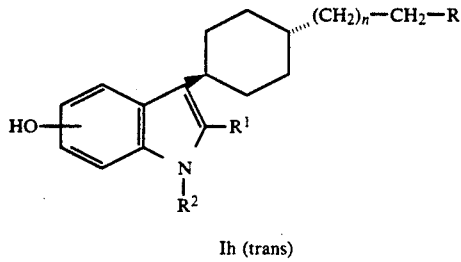

Ih (trans)

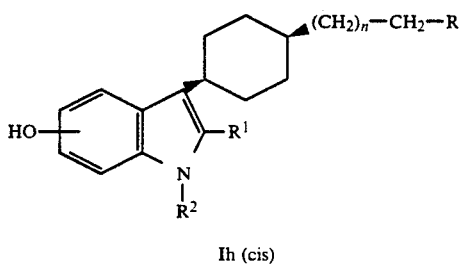

Ih (cis)

wherein $R^2$ is hydrogen, lower alkyl, or cycloalkyl and R, $R^1$, and n are as defined above or a pharmaceutically acceptable acid or base addition salt thereof is prepared as outlined in Scheme Iv.

Thus, a compound of Formula Ig (trans) or Formula Ig (cis) wherein $R^9$ is lower alkyl and R, $R^1$, $R^2$, and n are as defined above is reacted with pyridine hydrochloride and heated in a sealed tube to about 130° C. for about 3 days to afford a compound of Formula Ih (trans) or a compound of Formula Ih (cis), respectively. Preferably the reaction is carried out at 130° C. for 3 days.

A compound of Formula Ii (trans) or Formula Ii (cis)

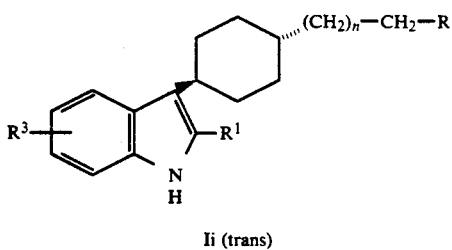

Ii (trans)

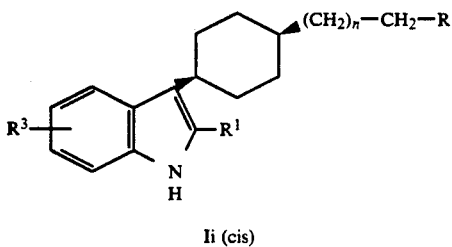

Ii (cis)

wherein R, $R^1$, $R^3$, and n are as defined above or a pharmaceutically acceptable acid or base addition salt thereof is prepared as outlined in Scheme V.

Thus, a compound of Formula V is reacted with the compound of Formula

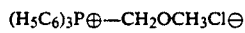

in the presence of a base such as, for example, n-butyl lithium and the like and a solvent such as, for example, tetrahydrofuran and the like to afford a compound of Formula XII wherein $R^1$ and $R^3$ are as defined above.

A compound of Formula XII is treated with an aqueous acid such as, for example, 10% aqueous hydrochloric acid and the like in the presence of a solvent such as, for example, tetrahydrofuran and the like to afford a compound of Formula XIVa wherein n is zero and $R^1$ and $R^3$ are as defined above.

Additionally, a compound of Formula V is reacted with a compound of Formula

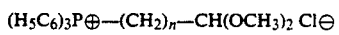

wherein n is 2 or 3 using the methodology used to prepare a compound of Formula XII from a compound of Formula V to afford a compound of Formula XIII wherein n is 2 or 3 and $R^1$ and $R^3$ are as defined above.

A compound of Formula XIII is treated with hydrogen int he present of a catalyst such as, for example, palladium on carbon and the like in a solvent such as, for example, methanol followed by subsequent treatment with an acid using the methodology used to convert a compound of Formula XII to a compound of Formula XIVa to afford a compound of Formula XIVb wherein n is 2 or 3 or $R^1$ and $R^3$ are as defined above.

A compound of Formula XIVa or Formula XIVb is treated with a compound of Formula A in the presence of a reducing agent such as, for example, sodium cyanoborohydride (NaCNB$_3$) and the like in a solvent such as, for example, acetonitrile and the like and a catalytic amount of acetic acid to afford a mixture of cis and trans isomers which are separated into the individual cis and trans isomers by conventional methodology as described above.

Compounds of Formula Ia (trans), Formula Ia (cis), Formula Ib (trans), Formula Ib (cis), Formula Ii (trans), and Formula Ii (cis) may be alkylated at the indole nitrogen with a compound of Formula B to afford N-alkylated derivatives using the methodology used to prepare a compound of Formula Ie (trans) or Formula Ie (cis) from a compound of Formula Id (trans) or Formula Id (cis).

Compound of Formulas A, B, and XI are either known or capable of being prepared by methods known in the art.

The compounds of the present invention can be prepared and administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg, according to the particular application and the potency of the active component. The composition can, if desired, also contain other compatible therapeutic agents.

In therapeutic use as antipsychotic agents, the compounds utilized in the pharmaceutical method of this invention are administered at the initial dosage of about 1 mg to about 50 mg per kilogram daily. A daily dose range of about 5 mg to about 25 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following nonlimiting examples illustrate the inventors' preferred compounds of the invention and methods for their preparation.

EXAMPLE 1

Trans
3-[4-[2-[4-[(2-pyridinyl)-1-piperazinyl]ethyl]cyclohexyl]-1H-indole

Step (a): Preparation of
4-(1H-3-indolyl)-3-cyclohexenone ethylene ketal

Indole (45.3 g, 0.38 mol), 1,4-cyclohexanedione monoethylene ketal (45.5 g, 0.29 mol) and potassium hydroxide (9.12 g, 0.16 mol) are heated to reflux in 100 mL of methanol for 18 hours. The reaction is cooled and the product is isolated by filtration and washed with water to give a white solid (69.0 g).

Step (b): preparation of 4-(1H-3-indolyl)cyclohexanone ethylene ketal 4-(1H-3-indolyl)-3-cyclohexenone ethylene ketal (66.6 g, 0.26 mmol) is dissolved in 500 mL of tetrahydrofuran and 100 mL of methanol, 1.0 g 5% palladium on carbon is added and the mixture is placed under 60 pounds per square inch (psi) of hydrogen. After 2 hours the reaction is filtered and concentrated to give the product as a tan solid (67.0 g). An analytical sample is recrystallized from methanol; mp 163°-5° C.

Step (c): preparation of 4-(1H-3-indolyl)cyclohexanone 4-(1H-3-indolyl)cyclohexanone ethylene ketal (66.4 g, 0.258 mol) is dissolved in 350 mL of acetone and 350 mL of 10% hydrochloric acid solution and allowed to stir at room temperature for 6 hours. The acetone is removed under reduced pressure and the mixture is made basic with concentrated ammonium hydroxide. The mixture is extracted with chloroform. The organic fraction is dried with sodium sulfate and volatiles are removed under reduced pressure. The resulting solid is taken up in hot ethyl acetate and upon cooling and filtration a crystalline solid is obtained (36.89 g).

Step (d): Preparation of Cis and Trans
2-(4-[1H-3-indolyl]cyclohexyl)acetic acid To a slurry of sodium hydride (8.60 g, 0.36 mol) in 230 mL of tetrahydrofuran at 0° C. is added triethyl phosphonoacetate (73.53 g, 0.328 mol) in 100 mL tetrahydrofuran. The reaction is allowed to come to room temperature and a solution of 4-(1H-3-indolyl)cyclohexanone (35.0 g, 0.164 mol) in 230 mL tetrahydrofuran is added. After 2 hours the reaction is quenched with 200 mL of saturated potassium dihydrogen phosphate (KH$_2$PO$_4$), the tetrahydrofuran is removed under reduced pressure and the resulting mixture is suspended in 200 mL saturated potassium dihydrogen phosphate (KH$_2$PO$_4$) and extracted with three 400 mL portions of ethyl acetate. The combined organic extracts are washed with brine, dried over sodium sulfate, and the solvents removed under reduced pressure. The resulting residue is dissolved in 600 mL of ethanol, treated with 5% palladium on carbon (5 g)) and placed under 50 psi of hydrogen gas. After the appropriate amount of hydrogen has been taken up the mixture is filtered, and the solvents removed under reduced pressure. The residue is redissolved in 250 mL of ethanol, and 100 mL of 10% sodium hydroxide solution is added. After 18 hours the ethanol is removed under reduced pressure. The aqueous mixture is extracted with ethyl acetate, the aqueous layer is then made acidic and extracted with three 300 mL portions of methylene chloride. The methylene chloride extracts are combined, dried with sodium sulfate, and evaporated to give the product (35.1 g). The product is isolated as a mixture of diastereomers (trans to cis 1.4:1).

Step (e): Preparation of Cis and Trans 1-(2-{4-[1H-3-indolyl]cyclohexyl}acetyl)-4-(2-pyridinyl)piperazine The mixture of cis and trans 2-(4-[1H-3-indolyl]cyclohexyl)acetic acids (5.0 g, 19.43 mmol) are suspended in 90 mL of methylene chloride (90 mL). Triethylamine is added (4.5 mL) and the resulting solution is cooled to 0° C. Isobutyl chloroformate (2.77 mL, 21.37 mmol) is added and the reaction is stirred for 120 minutes. A solution of 1-(2-pyridinyl)piperazine (3.49 g, 21.37 mmol) in methylene chloride is added and the reaction is allowed to stir at 0° C. for 3 hours and the reaction is then stirred at ambient temperature for 18 hours. A saturated solution of sodium bicarbonate (40 mL) is added and the organic phase is separated. The aqueous phase is extracted with two 90 mL portions of methylene chloride and the combined organic extracts are dried with sodium sulfate and evaporated. The residue is chromatographed on silica gel (2% methanol in chloroform) and 2 main fractions are isolated. The first fraction consists of trans 1-(2-{4-[1H-3-indolyl]cyclohexyl}acetyl)-4-(2-pyridinyl)piperazine and the second fraction consists of the corresponding cis isomer.

Step (f): Preparation of Trans 3-[4-[2-[4-(2-pyridinyl)-1-piperazinyl]ethyl]cyclohexyl]-1H-indole A slurry of lithium aluminum hydride (0.472 g, 12.4 mmol) in 20 mL of tetrahydrofuran at 0° C. is treated with aluminum chloride (0.553 g, 4.15 mmol) and the mixture is stirred for 20 minutes. A slurry of trans 1-(2-{4-[1H-3-indolyl]-cyclohexyl}acetyl)-4-(2-pyridinyl)-piperazine (1.67 g, 4.15 mmol) in 20 mL of tetrahydrofuran is added and the reaction is stirred at ambient temperature for 18 hours. Water (1 mL) and 10% sodium hydroxide solution (2 mL) is added the mixture is stirred for 2 hours, then filtered through celite and the volatiles are removed under reduced pressure. The resulting oil is triturated with diethyl ether to give the product as a white solid (1.57 g); mp 147°–148° C.

Following the procedure of Example 1, the following compounds are prepared:

EXAMPLE 2

Cis 3-[4-[2-[4-(2-pyridinyl)-1-piperazinyl]ethyl]cyclohexyl]-1H-indole; mp 99°–101° C.

EXAMPLE 3

Trans 3-[4-[2-[4-(2-pyrimidinyl)-1-piperazinyl]ethyl]cyclohexyl]-1H-indole, hydrochloride; mp 262° C. (dec).

EXAMPLE 4

Cis 3-[4-[2-[4-[(2-pyrimidinyl)-1-piperazinyl]ethyl]cyclohexyl]-1H-indole, hydrochloride; mp 145° C. (dec).

EXAMPLE 5

Trans 3-[4-[2-(3,6-dihydro-4-phenyl-1(2H);pyridinyl)ethyl]cyclohexyl]-1H-indole; mp 209°–210° C.

EXAMPLE 6

Cis 3-[4-[2-(3,6-dihydro-4-phenyl-1(2H-pyridinyl)ethyl]cyclohexyl]-1H-indole; mp 123°–124° C.

EXAMPLE 7

Trans 3-[4-[2-(3,6-dihydro-4-(2-thienyl)-1(2H)-pyridinyl)ethyl]cyclohexyl]-1H-indole; mp 192°–194° C.

EXAMPLE 8

Cis 3-[4-[2-(3,6-dihydro-4-(2-thienyl)-1(2H)pyridinyl)ethyl]cyclohexyl]-1H-indole; m/e 383.

EXAMPLE 9

Trans 3-[4-[2-(3,6-dihydro-4-(2-pyridinyl)-1(2H)-pyridinyl)ethyl]cyclohexyl]-1H-indole; m/e 383.

EXAMPLE 10

Cis 3-[4-[2-(3.6-dihydro-4-(2-pyridinyl)-1(2H)-pyridinyl)ethyl]cyclohexyl]-1H-indole; m/e 383.

EXAMPLE 11

Trans 5-methoxy-3-[4-[2-[4-(2-pyridinyl)-1-piperazinyl]ethyl]cyclohexyl]-1H-indole; m/e 418.

EXAMPLE 12

Cis 5-methoxy-3-[4-[2-[4-(2-pyridinyl)-1-piperazinyl]ethyl]cyclohexyl]-1H-indole; m/e 418.

EXAMPLE 13

Trans 5-fluoro-3-[4-[2-[4-(2-pyridinyl)-1-piperazinyl]ethyl]]cyclohexyl]-1H-indole.

EXAMPLE 14

Cis 5-fluoro-3-[4-[2-[4-(2-pyridinyl)-1-piperazinyl]ethyl]cyclohexyl]-1H-indole.

EXAMPLE 15

Trans 3-[4-[4-(2-pyridinyl)-1-piperazinyl methyl]cyclohexyl]-1H-indole and

EXAMPLE 15a

Cis 3-[4-[4-(2-pyridinyl)-1-piperazinylmethyl]cyclohexyl]-1H-indole

Method A

Step (a): Preparation of 4-(1H-3-indolyl)-cyclohexane carboxylic acid

To 50 mL of methanol is added sodium (3.32 g, 144.3 mmol). After the metal has dissolved indole (2.89 g, 24.6 mmol) and methyl 4-oxocyclohexanecarboxylate (5.0 g, 32.0 mmol) are added. The mixture is heated to reflux for 3 hours. The methanol is removed under reduced pressure and the residue partitioned between water and methylene chloride. The organic layer is discarded. The aqueous layer is acidified to pH 5 and extracted with three portions of methylene chloride. The combined organics are dried over sodium sulfate and evaporated to give 4-indolyl-3-cyclohexenecarboxylic acid (1.71 g). The material is hydrogenated in methanol (75 mL) under 50 psi of hydrogen int he presence of 5% palladium on carbon (0.5 g). After filtration and removal of solvent, the product is obtained as a mixture of diastereomers.

Step (b): Preparation of Trans 3-[4-[4-(2-pyridinyl)-1-piperazinylmethyl]cyclohexyl]-1H-indole and Cis 3-[4-[4-(2-pyridinyl)-1-piperazinylmethyl]cyclohexyl]-1H-indole A mixture of 4-(1H-3-indolyl)-cyclohexanecarboxylic acid (1.60 g, 6.57 mmol) and methylene chloride (30 mL) is treated with triethylamine (1.53 mL, 10.97 mmol) and the resulting solution is cooled to 0° C. Isobutyl chloroformate (0.93 mL, 7.15 mmol) is added and the reaction is stirred at 0° C. for 10 minutes. A solution of 1-(2-pyridinyl)piperazine (1.18 g, 7.23 mmol) in methylene chloride is added and the reaction is then stirred at ambient temperature for 18 hours. A saturated solution of sodium bicarbonate (20 mL) is added and the organic phase is separated. The aqueous phase is extracted with two 40 mL portions of methylene chloride and the combined organic extracts are dried with sodium sulfate, and evaporated. The residue is chromatographed on silica gel (2% methanol in chloroform) and 2 main fractions are isolated. The first fraction consisted of trans 1-({4-[1H-3-indolyl]cyclohexyl}carboxyl)-4-(2-pyridinyl)piperazine and the second fraction consisted of the corresponding cis isomer. The resulting trans amide is reduced by the method described in Example 1 to give trans 3-[4-[4-(2-pyridinyl)-1-piperazinylmethyl]-cyclohexyl]-1H-indole (Example 15); m/e 374.

Following the procedure of Example 15, cis 3-[4-[4-(2-pyridinyl)-1-piperazinylmethyl]cyclohexyl]-1H-indole (Example 15a) is obtained; m/e 374.

Method B

Step (a): preparation of Mixture of Cis and Trans 2-(4-[1H-3-indolyl]cyclohexyl]carboxaldehyde A mixture of (methoxymethyl)triphenylphosphonium chloride (10 g, 21.17 mmol) in 25 mL of tetrahydrofuran is cooled to −78° C. and treated with a 1.6M solution of butyllithium in hexanes (13.2 mL, 21.2 mmol). After 20 minutes a solution of 4-(1H-3-indolyl)-cyclohexanone (2.25 g, 10.6 mmol) in 25 mL of tetrahydrofuran is added. The reaction is warmed to 10° C. over 2 hours and then quenched with saturated ammonium chloride. The tetrahydrofuran is removed under reduced pressure and the resulting mixture is extracted with chloroform and dried over sodium sulfate. The solvents are removed under reduced pressure and the resulting residue is chromatographed on silica gel (1% methanol, 80% hexanes, 19% chloroform) to yield the corresponding methyl enol ether. The enol ether is hydrolyzed by heating in a solution of tetrahydrofuran and 10% hydrochloric acid for 2 hours. The tetrahydrofuran is removed under reduced pressure and the reaction mixture is partitioned between methylene chloride and water. The organic layer is dried and solvents are evaporated under reduced pressure to obtain the desired aldehyde as a 1:5 mixture of cis and trans isomers (1.37 g). the compound was characterized by proton NMR.

Step (b): preparation of Trans 3-[4-[4-(2-pyridinyl)-1-piperazinylmethyl]cyclohexyl]-1H-indole and Cis 3-[4-[4-(2-pyridinyl)-1-piperazinylmethyl]cyclohexyl]-1H-indole A mixture of cis and trans 2-(4-[1H-3-indolyl]cyclohexyl]carboxaldehyde (0.75 g, 3.3 mmol) and 2-pyridinyl piperazine (0.54 g, 3.3 mmol) are dissolved in 20 mL of acetonitrile, cooled to 0° C. and treated with 0.3 mL of acetic acid. The reaction is stirred for 15 minutes and is then treated with sodium cyanoborohydride (0.22 g, 3.5 mmol). The reaction is stirred for 3 hours, is diluted with water, the mixture is adjusted to pH 10 and extracted with chloroform. The chloroform extracts are dried with sodium sulfate and the solvents are evaporated under reduced pressure. The residue is chromatographed on silica gel (1% methanol, 99% chloroform) to give trans 3-[4-[4-(2-pyridinyl)-1-piperazinylmethyl]cyclohexyl]- 1H-indole (Example 15) (0.55 g) and cis 3-[4-[4-(2-pyridinyl)-1-pipeazinylmethyl]cyclohexyl]-1H-indole (Example 15a) (0.12 g).

EXAMPLE 16

3-[4-[2-[4-[(2-Pyridinyl)-1-piperazinyl]ethyl]cyclohexen-1-yl]-1H-indole

A mixture of 4-[2-[4-(2-pyridinyl)-1-piperazinyl]ethyl]cyclohexanone (Example A) (4.0 g, 13.91 mmol), indole (1.63 g, 13.91 mmol) and potassium hydroxide (0.198 g, 3.48 mmol) are heated in 20 mL of methanol for 14 hours. The methanol is evaporated under reduced pressure and the residue is partitioned between water and methylene chloride. The organic layer is dried with sodium sulfate and the solvent evaporated. The residue is chromatographed (2% methanol in chloroform 0.1% ammonia) and the major fraction is recrystallized with ethyl acetate to give the product as a white solid (1.49 g); mp 258°–260° C.

The cyclohexenyl compound may be hydrogenated in the presence of palladium on carbon to give a 1:1 mixture of diastereomers which are separated chromatographically to give both trans 3-[4-[2-[4-(2-pyridinyl)-1-piperazinyl]ethyl]cyclohexyl]-1H-indole (Example 1) and cis 3-[4-[2-[4-(2-pyridinyl)-1-piperazinyl]ethyl]cyclohexyl]-1H-indole (Example 2).

EXAMPLE 1

Trans
3-[4-[2-[4-(2-pyridinyl)-1-piperazinyl]ethyl]cyclohexyl]-1H-indol-5-ol

A mixture of trans 1-(2-{4-[1H-5-methoxy-3-indolyl]cyclohexyl}ethyl)-4-(2-pyridinyl)piperazine (Example 11) (2.0 g, 4.8 mmol) and pyridine hydrochloride (5.0 g, 43 mmol) is heated in a sealed tube to 130° C. for 3 days. The reaction is partitioned between chloroform and concentrated ammonium hydroxide. The organic layer is dried and solvents evaporated. The residue is chromatographed (3% methanol in chloroform containing 0.1% ammonia) to give the produce as a white solid; m/e 404.

Following the procedure of Example 17, the following compound is prepared:

EXAMPLE 18

Cis
3-[4-[2-[4-(2-pyridinyl)-1-piperazinyl]ethyl]cyclohexyl]-1H-indol-5-ol; m/e 404.

EXAMPLE 19

Trans
1-methyl-3-[4-[2-[4-(2-pyridinyl)-1-piperazinyl]ethyl]cyclohexyl]-1H-indole A mixture of potassium hydride (0.24 g, 6 mmol) in tetrahydrofuran is cooled to 0° C. and a solution of trans 1-(2-{4-[1H-3-indolyl]cyclohexyl}ethyl)-4-(2-pyridinyl)piperazine (Example 1) (2.0 g, 5.14 mmol) in 20 mL of tetrahydrofuran is added. After 20 minutes 3 mL of methyl iodide is added and the reaction is warmed to room temperature overnight. The reaction is quenched with ammonium chloride and the tetrahydrofuran is removed under reduced pressure. The residue is partitioned between chloroform and ammonium chloride and the organics are dried with sodium sulfate and solvents are evaporated. The residue is chromatographed on silica gel (2% methanol in chloroform) to give the desired product.

Following the procedure of Example 19, the following compound is prepared.

EXAMPLE 20

Cis
1-methyl-3-[5-[2-[4-(2-pyridinyl)-1-piperazinyl]ethyl]cyclohexyl-1H-indole

PREPARATION OF STARTING MATERIALS

EXAMPLE A

4-[2-[4-(2-Pyridinyl)1-piperazinyl]ethyl]cyclohexanone

Step (a): preparation of Ethyl 1,4-dioxaspiro[4,5]decane-8-acetate

A solution of triethyl phosphonoacetate (158.7 mL) in 500 mL of tetrahydrofuran is added over a period of 2 hours to an ice-cold suspension of 60% sodium hydride (38.5 g) in 500 mL of tetrahydrofuran under nitrogen. The reaction mixture is stirred at room temperature for 1 hours. A solution of 1,4-cyclohexanedione monoethylene ketal (100.0 g) in 500 mL of tetrahydrofuran is added dropwise and the reaction mixture is stirred at room temperature for 10 hours. The reaction is concentrated in vacuo and the residue taken up into ethyl acetate and washed with brine. The organic extract is dried (magnesium sulfate) and concentrated to leave 142.7 g of a light yellow liquid consisting of a mixture of isomeric unsaturated esters. A solution of these esters (1012.5 g) in 700 mL of ethanol containing 5 g of 5% palladium on charcoal is hydrogenated at 50 pounds per square inch (psi) ($H_2$) for 3 hours. The mixture is filtered and evaporated in vacuo. The title compound is obtained by distillation; $bp_1$ 110°–115° C.

Step (b): preparation of 1,4-Dioxaspiro[4,5]decane-8-acetic acid

A solution of ethyl 1,4-dioxaspiro[4,5]decane-8-acetate (50.0 g) in 50 mL of 4.8N sodium hydroxide solution and 400 mL of ethanol is refluxed under nitrogen for 2 hours. The mixture is concentrated in vacuo to remove the ethanol. The residue is acidified with a saturated sodium biphosphate solution and the mixture is extracted with ethyl acetate (2×300 mL). The organic extract is dried over magnesium sulfate, and evaporated in vacuo to give an oily solid which is triturated with hexane and filtered to give 38.25 g of the title compound as a white solid; mp 110°–113° C.

Step (c): preparation of 1-(1,4-Dioxaspiro[4,5]dec-8-ylacetyl)-4-(2-pyridinyl)piperazine An ice cold solution of 1,4-dioxaspiro[4,5]decane-8-acetic acid (20.0 g) and triethylamine (20.9 mL) in 100 mL of dichloromethane is treated dropwise with a solution of isobutyl chloroformate (19.4 mL) in 100 mL of dichloromethane under nitrogen. The resulting solution is stirred at 0° C. for 10 minutes and a solution of 1-(2-pyridiyl)piperazine (32.59 g) in 100 mL of dichloromethane is added dropwise. The mixture is stirred at 0° C. for 15 minutes and then at room temperature for 1 hour. After washing with 1L of a saturated solution of sodium bicarbonate, the organic phase is dried over magnesium sulfate and concentrated in vacuo. The crude product is purified by MPLC (medium pressure liquid chromatography) (silica; ethyl acetate) to give 25.50 g of the title compound as a colorless solid; mp 113°–116° C.

Step (d): preparation of 4-[2-[4-(2-Pyridinyl)-1-piperazinyl]ethyl]cyclohexanone A solution of 1-(1,4-dioxaspiro[4,5]dec-8-ylacetyl)-4-(2-pyridinyl)piperazine (17.0 g) in 500 mL of dry tetrahydrofuran is treated with sodium borohydride (6.81 g) under nitrogen and the resulting suspension is treated dropwise with a solution of boron trifluoride etherate (29.5 mL) in 100 mL of tetrahydrofuran. The reaction mixture is stirred at room temperature overnight. A solution of glacial acetic acid (10.3 mL) in 100 mL of tetrahydrofuran is added dropwise, and the mixture stirred at room temperature for 2 hours. The solvent is evaporated in vacuo and the residue refluxed with 250 mL of a 10% solution of hydrochloric acid and 250 mL of acetone for 2 hours. The mixture is concentrated in vacuo to about one-half of the original volume. The remaining aqueous solution is washed twice with ethyl acetate and made basic with ammonium hydroxide. The crude product is extracted into ethyl acetate (2×300 mL). the organic extract is dried over magnesium sulfate and concentrated in vacuo. The reaction mixture is purified by MPLC (silica; 2% methanol, 98% chloroform) to give 9.73 g of the title compound as a colorless solid; mp 104°–106° C.

We claim:
1. A compound of Formula I:

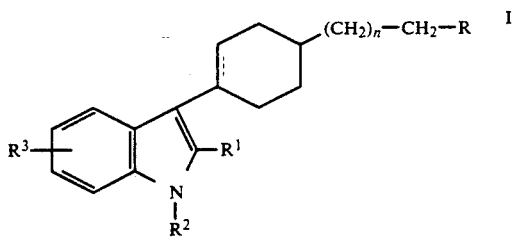

wherein
R is

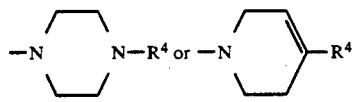

wherein R⁴ is aryl, unsubstituted or substituted by one to four substituents selected from lower alkyl, lower alkoxy, lower thioalkoxy, hydroxy, lower acyloxy, amino,

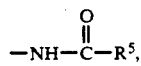

wherein R⁵ is lower alkyl, halogen, or trifluoromethyl, 2-k 3-, or 4-pyridinyl, unsubstituted or substituted by halogen, lower alkyl, hydroxy, lower acyloxy, lower alkoxy, amino, or

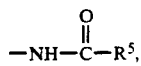

wherein R⁵ is as defined above, 2-, 4-, or 5-pyrimidinyl, unsubstituted or substituted by halogen, lower alkyl, hydroxy, lower acyloxy, lower alkoxy, amino, or

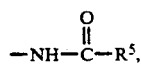

wherein R⁵ is as defined above, 2-pyrazinyl, unsubstituted or substituted by halogen, lower alkyl, hydroxy, lower acyloxy, lower alkoxy, amino, or

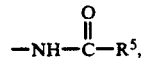

wherein R⁵ is as defined above, 2- or 3-furanyl, unsubstituted or substituted by halogen, lower alkyl, hydroxy, lower acyloxy, lower alkoxy, amino, or

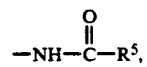

wherein R⁵ is as defined above, 2-, or 3-thienyl, unsubstituted or substituted by halogen, lower alkyl, hydroxy, lower acyloxy, lower alkoxy, amino, or

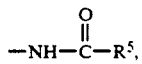

wherein R⁵ is as defined above, 2-, 4-, or 5-imidazolyl, unsubstituted or substituted by halogen, lower alkyl, hydroxy, lower acyloxy, lower alkoxy, amino, or

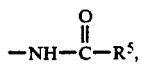

wherein R⁵ is as defined above, 2-, 4-, or 5-thiazolyl, unsubstituted or substituted by halogen, lower alkyl, hydroxy, lower acyloxy, lower alkoxy, amino, or

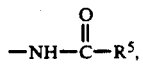

wherein R⁵ is as defined above, or 2-, 3-, 4-, 5-, 6-, or 7-indolyl, unsubstituted or substituted by halogen, lower alkyl, hydroxy, lower acyloxy, lower alkoxy, amino, or

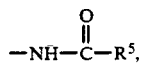

wherein R⁵ is as defined above;
R¹ is hydrogen, —CN, or —CO₂H;
R² is hydrogen, lower alkyl, or cycloalkyl;
R³ is hydrogen, halogen, hydroxyl, lower alkoxy, lower alkyl,

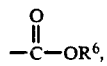

wherein R⁶ is hydrogen or lower alkyl,

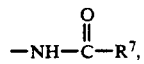

wherein R⁷ is hydrogen, lower alkyl, cycloalkyl, or aryl, unsubstituted or substituted by one to four substituents selected from lower alkyl, lower alkoxy, lower thioalkoxy, hydroxy, lower acyloxy, amino,

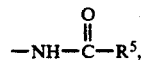

wherein R⁵ is as defined above, halogen, or trifluoromethyl,

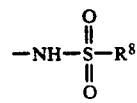

wherein R⁸ is lower alkyl, cycloalkyl or aryl, unsubstituted or substituted by one to four substituents selected from lower alkyl, lower alkoxy, lower thioalkoxy, hydroxy, lower acyloxy, amino,

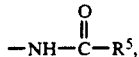

wherein $R^5$ is as defined above, halogen, or trifluoromethyl, or
—NH$_2$;
n is zero or an integer of 1, 2, or 3;
≕ is a single or double bond; and corresponding geometric isomers thereof; or a pharmaceutically acceptable acid or base addition salt thereof.

2. A compound according to claim 1, in which $R^4$ is aryl, unsubstituted or substituted by one to four substituents selected from lower alkyl, lower alkoxy, lower thioalkoxy, hydroxy, lower acyloxy, amino,

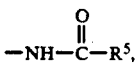

wherein $R^5$ is lower alkyl, halogen, or trifluoromethyl, 2-, 3-, or 4-pyridinyl, 2-, 4-, or 5-pyrimidinyl, 2-, or 3-furanyl, 2-, or 3-thienyl, 2-, 4-, or 5-thiazolyl, or 2-, 3-, 4-, 5-, 6-, or 7-indolyl,.

3. A compound according to claim 2, in which $R^4$ is aryl, 2-, 3-, or 4-pyridinyl, 2-, 4-, or 5-pyrimidinyl, 2-, or 3-furanyl, 2-, or 3-thienyl, 2-, 4-, or 5-thiazolyl, or 2-, 3-, 4-, 5-, 6-, or 7-indolyl.

4. A compound according to claim 1 selected from the group consisting of:
Trans 3-[4-[2-[4-(2-pyridinyl)-1-piperazinyl]ethyl]cyclohexyl]-1H-indole;
Cis 3-[4-[2-[4-(2-pyridinyl)-1-piperazinyl]ethyl]cyclohexyl]-1H-indole;
Trans 3-[4-[2-[4-(2-pyrimidinyl)-1-piperazinyl]ethyl]cyclohexyl]-1H-indole, hydrochloride;
Cis 3-[4-[2-(2-pyrimidinyl)-1-piperazinyl]ethyl]cyclohexyl]-1H-indole, hydrochloride;
Trans 3-[4-[2-(3,6-dihydro-4-phenyl-1(2H)-pyridinyl)ethyl]cyclohexyl]-1H-indole;
Cis 3-[4-[2-(3,6-dihydro-4-phenyl-1(2H)-pyridinyl)ethyl]cyclohexyl]-1H-indole;
Trans 3-[4-[2-(3,6-dihydro-4-(2-thienyl)-1(2H)-pyridinyl)ethyl]cyclohexyl]-1H-indole;
Cis 3-[4-[2-(3,6-dihydro-4-(2-thienyl)-1(2H)-pyridinyl)ethyl]cyclohexyl]-1H-indole.
Trans 3-[4-[2-(3,6-dihydro-4-(2-pyridinyl)-1(2H)-pyridinyl)ethyl]cyclohexyl]-1H-indole.
Cis 3-[4-[2-(3,6-dihydro-4-(2-pyridinyl)-1(2H)-pyridinyl)ethyl]cyclohexyl]-1H-indole;
Trans 5-methoxy-3-[4-[2-[4-(2-pyridinyl)-1-piperazinyl]ethyl]cyclohexyl]-1H-indole.
Cis 5-methoxy-3-[4-[2-[4-(2-pyridinyl)-1-piperazinyl]ethyl]cyclohexyl]-1H-indole;
Trans 5-fluoro-3-[4-[2-[4-(2-pyridinyl)-1-piperazinyl]ethyl]cyclohexyl]-1H-indole;
Cis 5-fluoro-3-[4-[2-[4-(2-pyridinyl)-1-piperazinyl]ethyl]cyclohexyl]-1H-indole;
Trans 3-[4-[4-(2-pyridinyl)-1-piperazinylmethyl]cyclohexyl]-1H-indole;
Cis 3-[4-[4-(2-pyridinyl)-1-piperazinylmethyl]cyclohexyl]-1H-indole.
3-[4-[2-[4-[(2-Pyridinyl)-1-piperazinyl]ethyl]cyclohexen-1-yl]-1H-indole;
Trans 3-[4-[2-[4-(2-pyridinyl)-1-piperazinyl]ethyl]cyclohexyl]-1H-indol-5-ol;
Cis 3-[4-[2-[4-(2-pyridinyl)-1-piperazinyl]ethyl]cyclohexyl]-1H-indol-5-ol;
Trans 1-methyl-3-[4-[2-[4-(2-pyridinyl)-1-piperazinyl]ethyl]cyclohexyl]-1H-indole; and
Cis 1-methyl-3-[4-[2-[4-(2-pyridinyl)-1-piperazinyl]ethyl]cyclohexyl]-1H-indole.

5. A method of treating schizophrenia comprising administering to a host suffering therefrom a therapeutic effective amount of a compound according to claim 1 in unit dosage form.

6. A method of treating depression comprising administering to a host suffering therefrom a therapeutic effective amount of a compound according to claim 1 in unit dosage form.

7. A pharmaceutical composition adapted for administration as a dopaminergic, antipsychotic, or antidepressant agent comprising a therapeutic effective amount of a compound according to claim 1 in admixture with a pharmaceutically acceptable excipient, diluent, or carrier.

* * * * *

UNITED STATES PATENT AND TRADEMARK OFFICE
CERTIFICATE OF CORRECTION

PATENT NO.   : 5,124,332
DATED        : June 23, 1992
INVENTOR(S)  : Wise, L. D., et al It is certified that error appears in the above-indentified patent and that said Letters Patent is hereby corrected as shown below:

```
At column 33, line 31,
    delete "k"
    insert ",".

At column 35, line 39,
    after "Cis    3-[4-[2-"
    insert "[4-".
```

Signed and Sealed this

Twenty-fourth Day of August, 1993

Attest:

BRUCE LEHMAN

Attesting Officer

Commissioner of Patents and Trademarks